US008860442B2

(12) United States Patent
Je et al.

(10) Patent No.: US 8,860,442 B2
(45) Date of Patent: Oct. 14, 2014

(54) METHOD OF DETERMINING A SENSITIVITY OF A BIOSENSOR ARRANGEMENT, AND BIOSENSOR SENSITIVITY DETERMINING SYSTEM

(75) Inventors: Minkyu Je, Singapore (SG); Guo-Jun Zhang, Singapore (SG); Tshun Chuan Chai, Singapore (SG); Cheng Fang, Singapore (SG)

(73) Assignee: Agency for Science, Technology and Research (SG)

( * ) Notice: Subject to any disclaimer, the term of this patent is extended or adjusted under 35 U.S.C. 154(b) by 948 days.

(21) Appl. No.: 12/878,234

(22) Filed: Sep. 9, 2010

(65) Prior Publication Data

US 2011/0062972 A1 Mar. 17, 2011

Related U.S. Application Data

(60) Provisional application No. 61/241,572, filed on Sep. 11, 2009.

(51) Int. Cl.
*G01R 27/08* (2006.01)
*G01N 27/414* (2006.01)

(52) U.S. Cl.
CPC .................................. *G01N 27/4145* (2013.01)
USPC .......................................................... 324/692

(58) Field of Classification Search
None
See application file for complete search history.

(56) References Cited

U.S. PATENT DOCUMENTS 4,385,274 A * 5/1983 Shimada et al. ............. 324/71.6
4,478,222 A 10/1984 Koning et al.

5,132,000 A 7/1992 Sone et al.
5,911,873 A 6/1999 McCarron et al.
7,019,305 B2 3/2006 Eversmann et al.

FOREIGN PATENT DOCUMENTS

DE 10025580 12/2001
JP 2003014684 A * 1/2003

OTHER PUBLICATIONS

N. Gemma, S. O'uchi, H. Funaki, J. Okada and S. Hongo, "CMOS integrated DNA chip for quantitative DNA analysis," ISSCC Dig. Tech. Papers, pp. 560-561, Feb. 2006.

(Continued)

*Primary Examiner* — Paresh Patel
(74) *Attorney, Agent, or Firm* — Altera Law Group, LLC

(57) ABSTRACT

According to an embodiment of the present invention, a method of determining or adjusting the sensitivity of a biosensor arrangement comprising at least one field effect biosensor is provided, each of the at least one field effect biosensor comprising: a semiconductor substrate comprising a source region, a drain region and a channel region disposed between the source region and the drain region; a gate isolation layer covering the channel region; and a reference electrode disposed over the gate isolation layer such that a electrolytic solution to be sensed can be provided between the reference electrode and the gate isolation layer. The method comprises the following processes carried out for each field effect biosensor: providing an electrolytic solution between the reference electrode and the gate isolation layer; applying a source/drain voltage between the source region and the drain region; varying a reference voltage supplied to the reference electrode over a voltage range; measuring a resulting drain current while varying the reference voltage in order to obtain a corresponding drain current function; and determining the sensitivity of the field effect biosensor based on the reference voltage supplied to the reference electrode and the corresponding drain current function.

16 Claims, 13 Drawing Sheets

(56) References Cited

OTHER PUBLICATIONS

M. J. Milgrew, D. R. S. Cumming, IEEE Trans. Electron Devices, vol. 55, p. 1074, 2008.

G. Ferrari, F. Gozzini and M. Sampietro, "A current-sensitive front-end amplifier for nano-biosensors with a 2MHz BW," ISSCC Dig. Tech. Papers, pp. 164-165, Feb. 2007.

F. Seker, K. Meeker, T. F. Kuech, A. B. Ellis, Chem. Rev., vol. 100, p. 2505, 2000.

M. Bennati, F. Thei, M. Rossi, M. Crescentini, G. D'Avino, A. Baschirotto and M. Tartagni, "A sub-pA ΔΣ current amplifier for single-molecule nanosensors," ISSCC Dig. Tech. Papers, pp. 348-349, Feb. 2009.

S. J. Tans, A. R. M. Verschueren, C. Dekker, Nature, vol. 393, p. 49, 1999.

U. Frey, F. Heer, R. Pedron, S. Hafizovic, F. Greve, J. Sedivy, K.-U. Kirstein and A. Hierlemann, "An 11k-electrode 126-channel high-density microelectrode array to interact with electrogenic cells," ISSCC Dig. Tech. Papers, pp. 158-159, Feb. 2007.

P. G. Collins, M. S. Arnold, P. Avouris, Science, vol. 292, p. 706, 2001.

N. Lei, B. O. Watson, J. N. MacLean, R. Yuste and K. L. Shepard, "A 256×256 CMOS microelectrode array for extracellular neural stimulation of acute brain slices," ISSCC Dig. Tech. Papers, pp. 148-149, Feb. 2008.

Y. Cui, X. Duan, J. Hu, C. M. Lieber, J. Phys. Chem. B, vol. 104, p. 5213, 2000.

Y. Cui, C. M. Lieber, Science, vol. 291, p. 851, 2001.

X. Duan, Y. Huang, Y. Cui, J. Wang, C. M. Lieber, Nature, vol. 409, p. 66, 2001.

J. J. Gooding, Small, vol. 2, p. 313, 2006.

P. Bergveld, IEEE Trans. Biomed. Eng., vol. BME-19, p. 342, 1972.

M. Abe, K. Murata, T. Ataka, K. Matsumoto, Nanotechnology, vol. 19, 2008.

L. Bousse, J. Chem. Phys., vol. 76, p. 5128, 1982.

D. Landheer, G. Aers, W. R. McKinnon, M. J. Deen, J. C. Ranuarez, J. Appl. Phys., vol. 98, p. 044701, 2005.

G-J Zhang, J. H. Chua, R-E. Chee, A. Agarwal, S. M. Wong, K. D. Buddharaju, N. Balasubramanian, Biosens. Bioelectron., vol. 23, p. 1701, 2008.

\* cited by examiner

US 8,860,442 B2

METHOD OF DETERMINING A SENSITIVITY OF A BIOSENSOR ARRANGEMENT, AND BIOSENSOR SENSITIVITY DETERMINING SYSTEM

CROSS REFERENCE TO RELATED APPLICATION

This application claims priority to U.S. provisional application No. 61/241,572 filed on 11 Sep. 2009, the content of which is incorporated herein by reference in its entirety for all purposes.

BACKGROUND

The present invention relates generally to a method of determining a sensitivity of a biosensor arrangement, and a biosensor sensitivity determining system.

Field-effect semiconductor devices can serve as a basis for chemical and biological sensors. In such a sensor, the presence of chemical or biological substances changes the conductance of the field-effect semiconductor device. Thus, the amount of change of conductance reflects the amount of chemical or biological substances put onto the sensor.

For example, a planar field effect transistor (FET) can be configured as a chemical or biological sensor by modifying the gate dielectric (on which no gate electrode is present) with molecular receptors or a selective membrane for the analyte of interest. The binding of a charged species to the molecular receptors then results in depletion or accumulation of carriers within the transistor structure, see for example document "P. Bergveld, *IEEE Trans. Biomed. Eng.*, vol. BME-19, p. 342, 1972".

Different ways of calibrating such a sensor are known. For example, in document "M. Abe, K. Murata, T. Ataka, K. Matsumoto, *Nanotechnology*, vol. 19, 2008", a calibration technique is presented in which a set of test solutions having different concentrations of target species is used to construct normalized characteristic curves for the sensor. This approach might be useful for certain applications such as pH and ion concentration measurement that detects reversible process. However, it cannot be used for detection of antibody-antigen binding process, for example, which is practically irreversible due to the extremely small dissociation constant of the process. Moreover, considering that a whole set of test solutions has to be prepared for calibration curve construction and the calibration should be performed for every single biosensor chip, this method is expensive and not suitable for point-of-care applications where the cost effectiveness is very important.

It would be desirable to provide a calibration method of chemical or biological sensors which is applicable to both reversible and irreversible processes and only needs minimal effort to be carried out.

SUMMARY OF THE INVENTION

The invention provides a method of determining or adjusting the sensitivity of a biosensor arrangement comprising at least one field effect biosensor, each of the at least one field effect biosensor comprising: a semiconductor substrate comprising a source region, a drain region and a channel region disposed between the source region and the drain region; a gate isolation layer covering the channel region; and a reference electrode disposed over the gate isolation layer such that a electrolytic solution to be sensed can be provided between the reference electrode and the gate isolation layer. The method comprises the following processes carried out for each field effect biosensor: providing an electrolytic solution between the reference electrode and the gate isolation layer; applying a source/drain voltage between the source region and the drain region; varying a reference voltage supplied to the reference electrode over a voltage range; measuring a resulting drain current while varying the reference voltage in order to obtain a corresponding drain current function; and determining the sensitivity of the field effect biosensor based on the reference voltage supplied to the reference electrode and the corresponding drain current function.

The invention further provides a biosensor sensitivity determining system for determining or adjusting the sensitivity of a biosensor arrangement comprising at least one field effect biosensor, each of the at least one field effect biosensor comprising: a semiconductor substrate comprising a source region, a drain region and a channel region disposed between the source region and the drain region; a gate isolation layer covering the channel region; and a reference electrode disposed over the gate isolation layer such that a electrolytic solution to be sensed can be provided between the reference electrode and the gate isolation layer. The biosensor sensitivity determining system comprises the following functional units for each of the field effect biosensors: a source/drain voltage applying unit adapted to apply a source/drain voltage between the source region and the drain region; a reference voltage applying unit adapted to apply a varying reference voltage which varies over a predetermined voltage range to the reference electrode; a drain current measuring unit adapted to measure a drain current resulting when varying the reference voltage in order to obtain a corresponding drain current function; and a sensitivity determining unit adapted to determine the sensitivity based on the reference voltage supplied to the corresponding reference electrode and the corresponding drain current function.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1A:
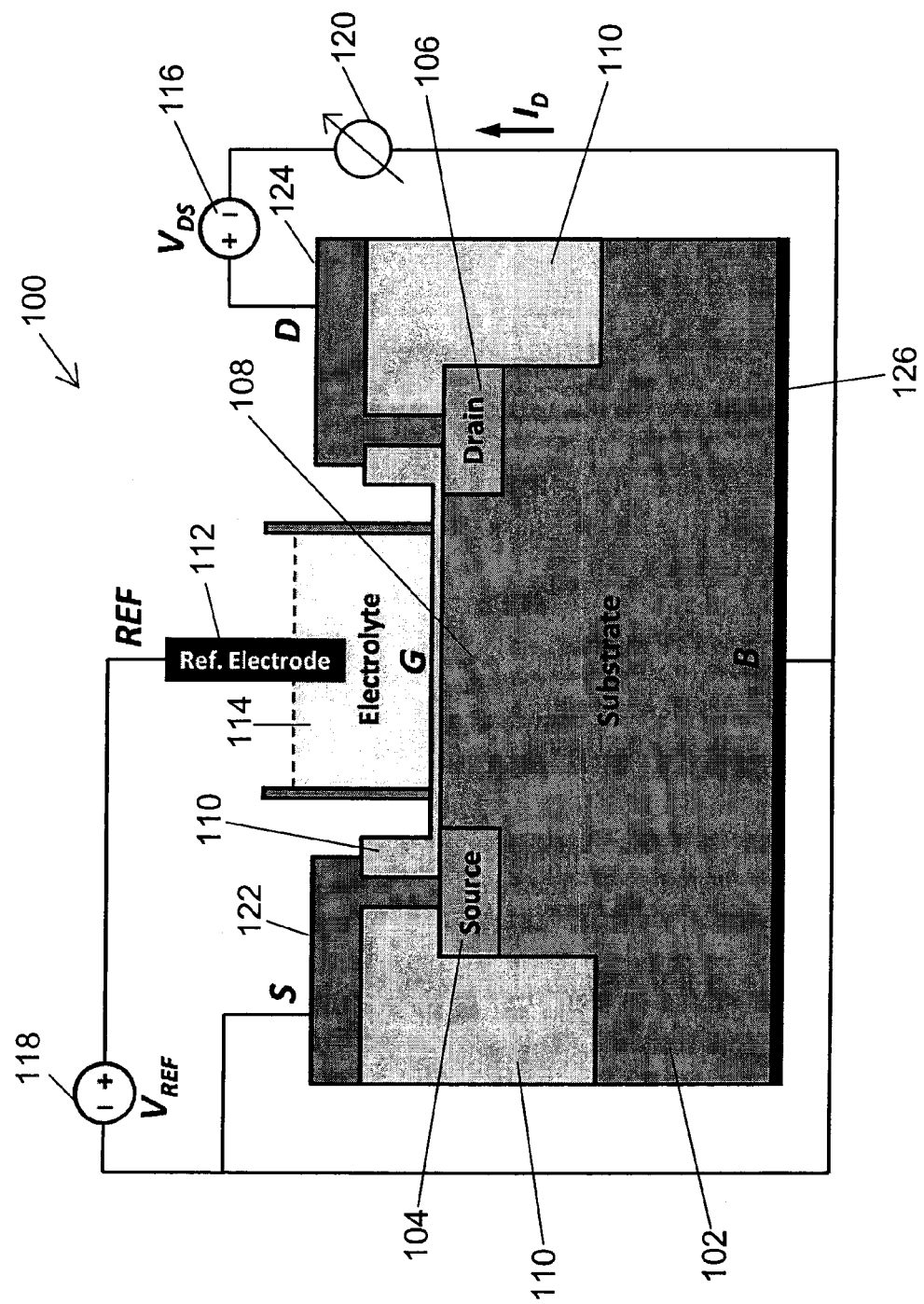
FIG. 1A shows a schematic view of a biosensor which may be calibrated according to an embodiment.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

In the scope of the present invention, the term "biological sensor" also includes the meaning of a chemical sensor. That is, the "biological sensor" according to the present invention may sense biological material as well as chemical material.

FIG. 1 shows a biosensor 100, the sensitivity of which can be determined or adjusted according to embodiments of the present invention. The biosensor comprises a field effect transistor. The field effect transistor comprises: a semiconductor substrate 102 comprising a source region 104, a drain region 106 and a channel region 108 disposed between the source region 104 and the drain region 106; a gate isolation layer 110 covering the channel region 108; and a reference electrode 112 disposed over the gate isolation layer 110 such that an electrolytic solution 114 to be sensed can be provided between the reference electrode 112 and the gate isolation layer 110. The biosensor further comprises a source/drain voltage applying unit 116 adapted to apply a source/drain voltage $V_{DS}$ between the source region 104 and the drain region 106 and a reference voltage applying unit 118 adapted to apply a reference voltage $V_{REF}$ (gate voltage) to the reference electrode 112. Further, the biosensor comprises a source/drain current measuring unit 120 which measures a source/drain current $I_D$. The source region 104 is connected via a source contact 122 to a first terminal of the reference voltage applying unit 118, and the reference electrode is connected to a second terminal of the reference voltage applying unit 118. The drain region 106 is connected via a drain contact 124 to a first terminal of the source/drain voltage applying unit 116. A second terminal of the source/drain voltage applying unit 116 is connected to a first terminal of the source/drain current measuring unit 120. A second terminal of the source/drain current measuring unit 120 is connected to the first terminal of the reference voltage applying unit 118 and to a bulk electrode 126 provided on the bottom surface of the substrate 102.

The biosensor 100 works as follows: An substance to be examined in put on the gate isolation layer 110 such that the bottom part of the reference electrode reaches into the substance. Then, the reference voltage $V_{REF}$ is applied to the reference electrode 112. Depending on the substance, the strength of the source/drain current $I_D$ will vary (This is due to the fact that the gate insulation layer 110 is covered by a cover layer 128 (not shown in FIG. 1) comprising receptors adapted to bind a particular kind of molecules ("target molecules")). If the substance to be analyzed comprises such molecules, the influence of the effective charge of the molecules on the channel region 108 is different, compared to the case where the molecules do not correspond to the receptors). The strength of the source/drain current $I_D$ therefore indicates which substance has been put onto the gate isolation layer 110, i.e. indicates whether the substance to be analyzed comprises the target molecules or not.

Figure 1B:
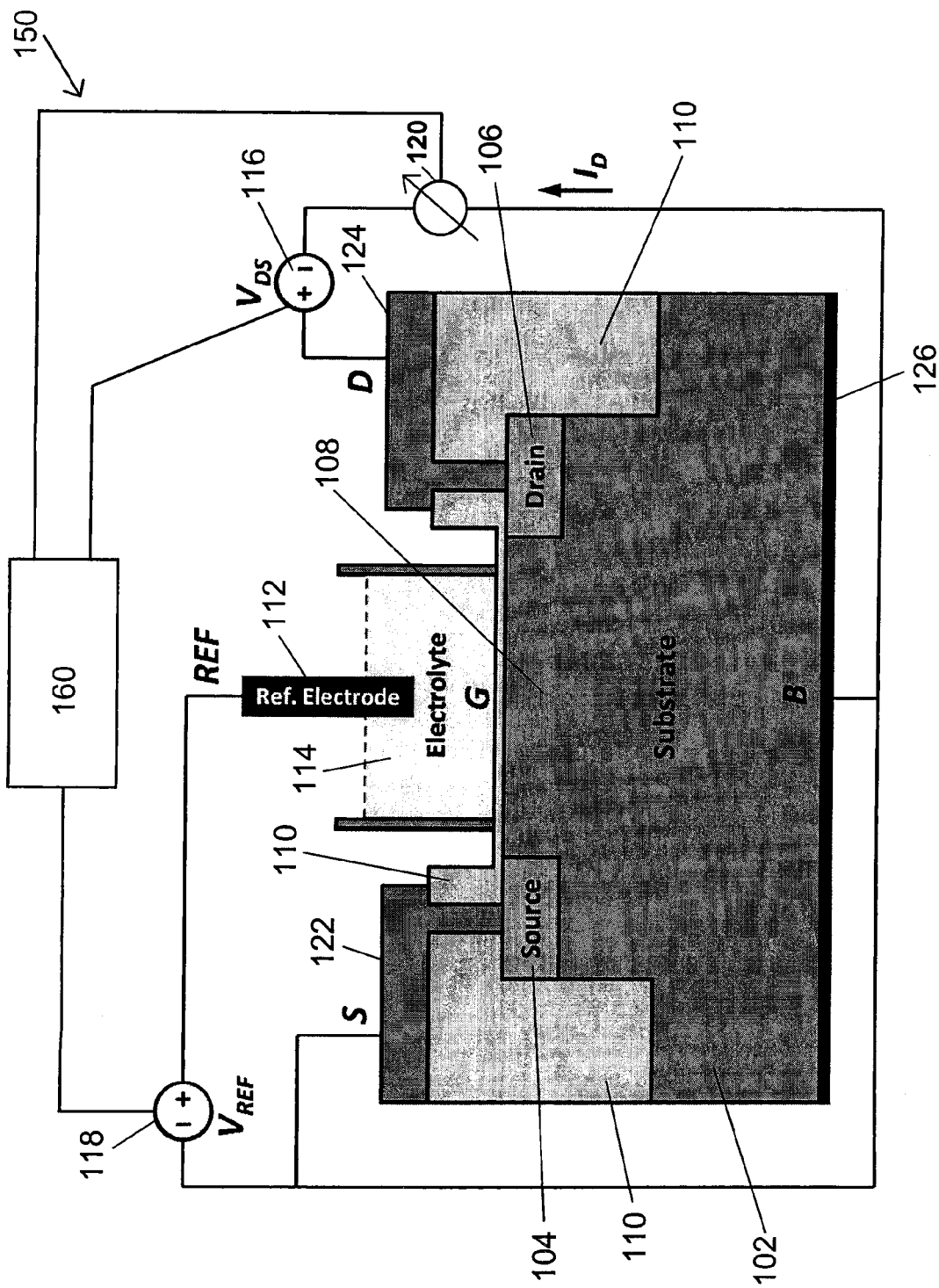
FIG. 1B shows a schematic view of a biosensor sensitivity determining system according to an embodiment of the present invention which uses a biosensor according to FIG. 1A.

FIG. 1B shows a biosensor sensitivity determining system 150 according to one embodiment of the present invention which determines the sensitivity of the biosensor 100. The biosensor sensitivity determining system 150 comprises a controlling/processing unit 160 which is connected to the reference voltage applying unit 118, the source/drain voltage applying unit 116, and the drain region 106. The controlling/processing unit 160 controls the reference voltage applying unit 118, the source/drain voltage applying unit 116, and the drain region 106 in the following manner: The reference voltage $V_{REF}$ is varied while the a source/drain voltage $V_{DS}$ is kept constant. The controlling/processing unit 160 then monitors the resulting source/drain current $I_D$ and calculates the sensitivity based on the variation of the reference voltage $V_{REF}$ and the corresponding source/drain current $I_D$.

Figure 2:
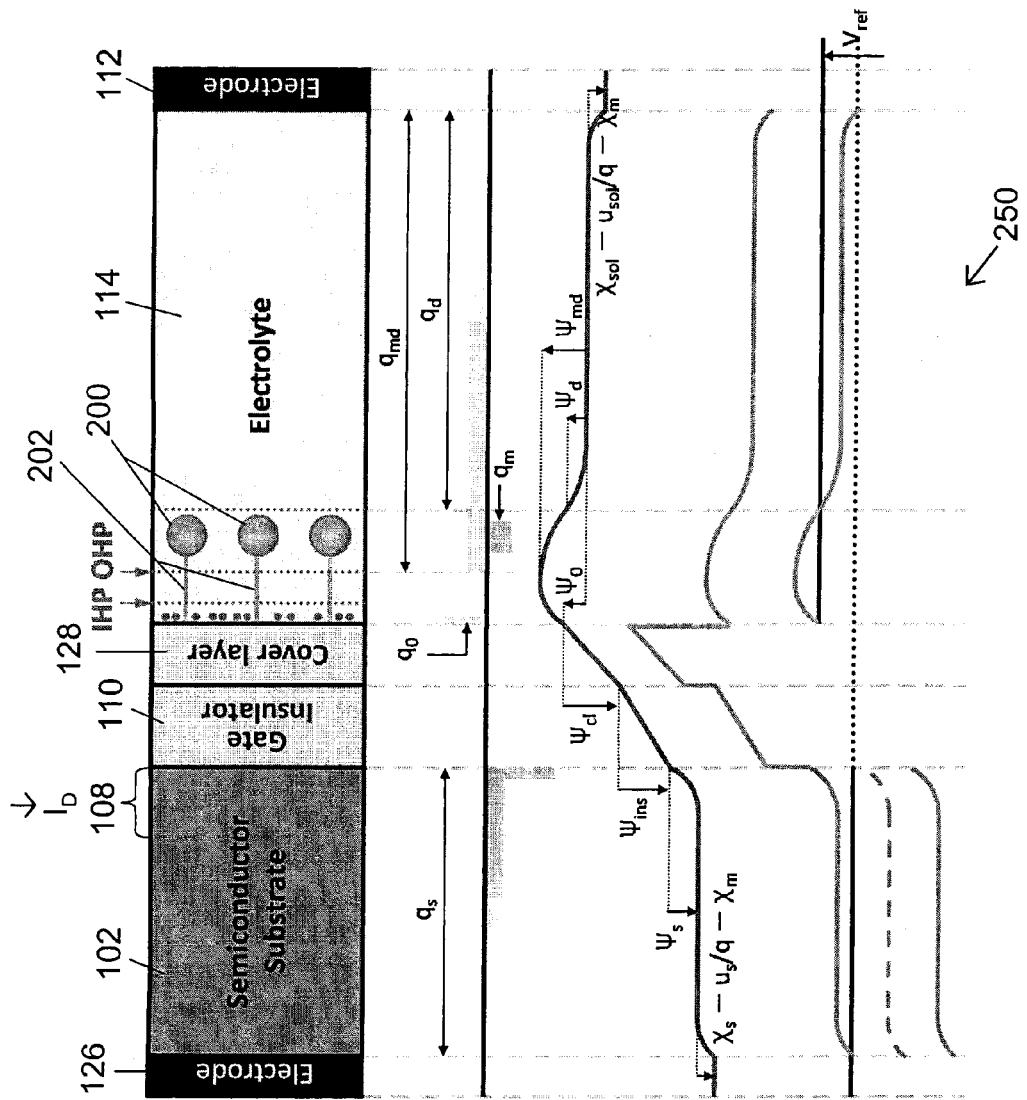
FIG. 2 shows an energy band diagram and charge distribution occurring in the biosensor shown in FIG. 1A.

FIG. 2 shows a corresponding energy band diagram and charge distribution 250 occurring in the biosensor 100 shown in FIG. 1. As can be derived from FIG. 2, the binding of target molecules 200 to the receptors located on the cover layer 128 generates an amount of charge $q_m$ which influences the energy band structure, in particular within the channel region 108. This change in the energy band structure can be detected by the change of the source/drain current $I_D$ routed through the channel region 108. Aspects of FIG. 2 will be explained later in more detail.

Figure 3:
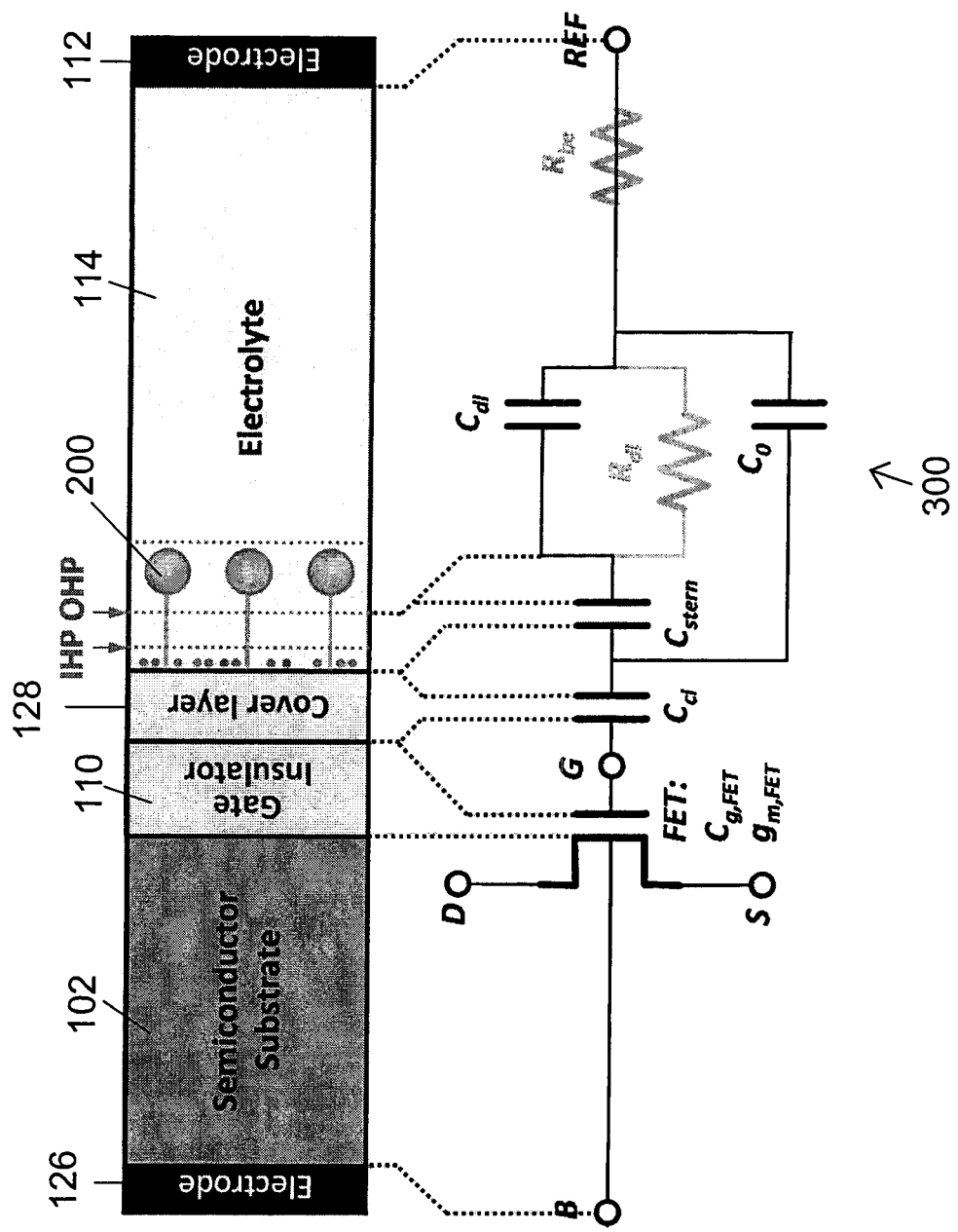
FIG. 3 shows an equivalent circuit of the biosensor shown in FIG. 1A.

FIG. 3 shows an equivalent circuit 300 of the biosensor 100 shown in FIG. 1. As can be derived from FIG. 3, the effect of electrolyte 114 on the channel region 108 can be modeled by an arrangement of capacitors and resistors. Aspects of FIG. 3 will be explained later in more detail.

Figure 4:
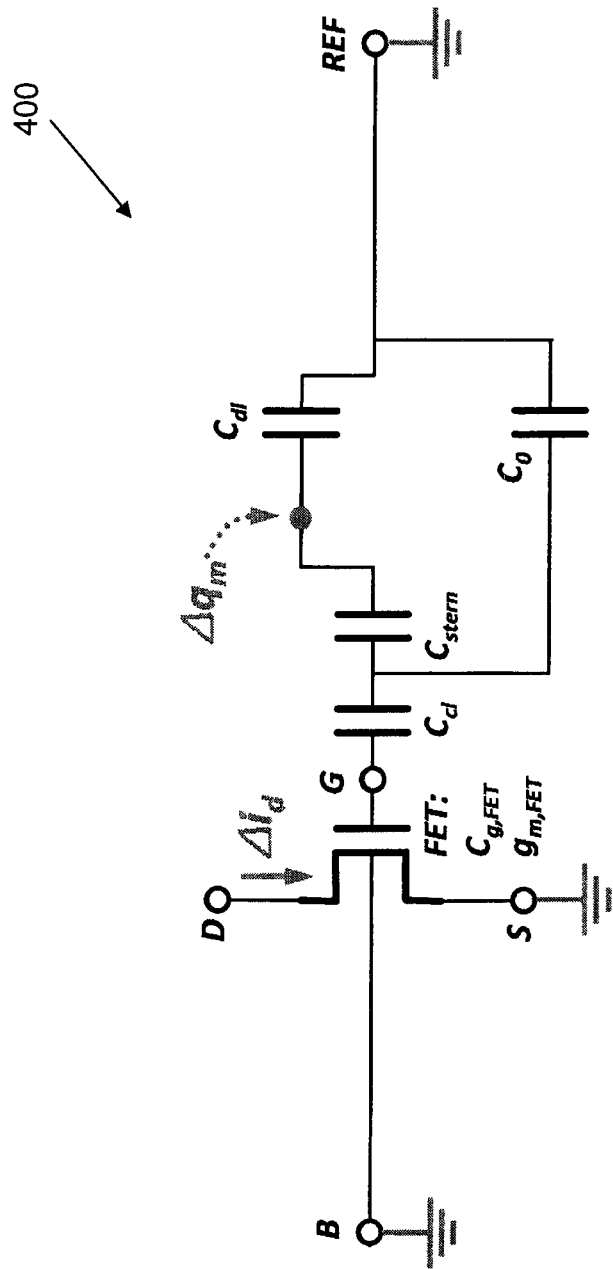
FIG. 4 shows an equivalent circuit of the biosensor illustrating the case where a sensitivity of the biosensor with regard to a change of molecular charge is determined.

FIG. 4 shows an equivalent circuit 400 of the biosensor 100 illustrating the case where a sensitivity $S_{qm}$ of the biosensor 100 with regard to a change of molecular charge $\Delta q_m$ is determined. This is a conventional way of determining the sensitivity of the biosensor 100: a change of charge $\Delta q_m$ is induced by providing a known testing substance onto the cover layer 128 (the effective charge of molecules of the testing substance effect the change of charge $\Delta q_m$). The change of charge $\Delta q_m$ effects a change of the source/drain current $\Delta I_D$ routed through the channel region 108. In this way, the sensitivity of the biosensor 100 on the testing substance can be examined.

Figure 5:
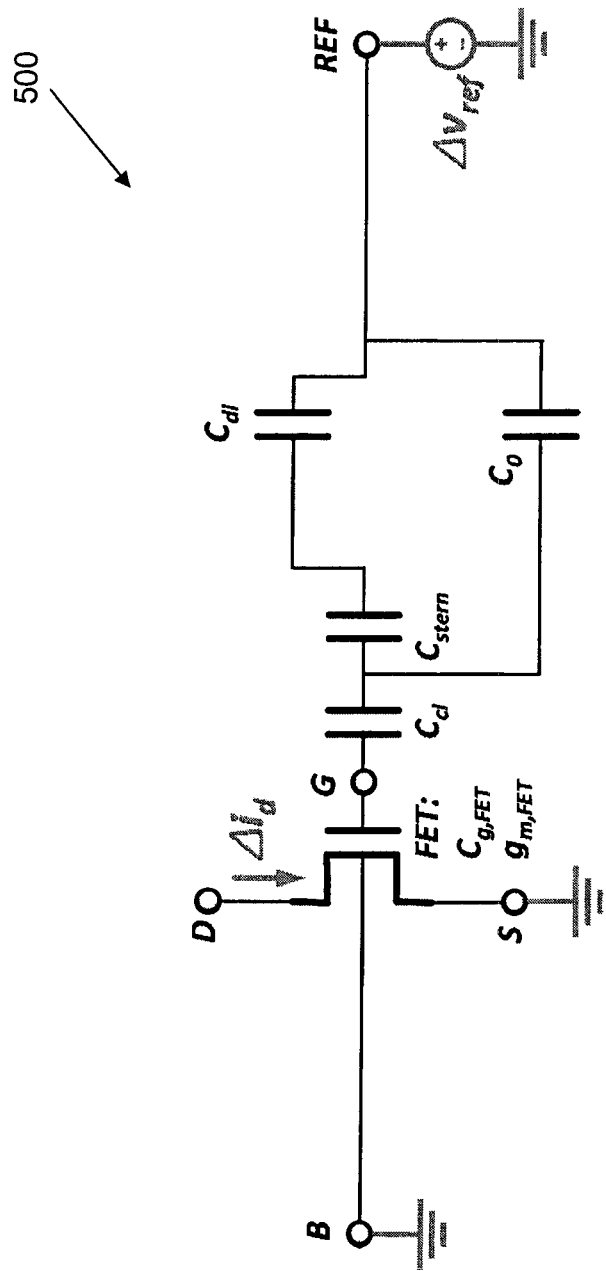
FIG. 5 shows an equivalent circuit of the biosensor illustrating the case where a sensitivity of the biosensor with regard to a change of the reference voltage is determined according to an embodiment of the present invention.

FIG. 5 shows an equivalent circuit 500 of the biosensor 100 illustrating the case where a sensitivity $S_{cal}$ of the biosensor 100 with regard to a change of the reference voltage $\Delta V_{REF}$ is determined: a change of the reference voltage $\Delta V_{REF}$ effects a change of the source/drain current $\Delta I_D$ routed through the channel region 108. This approach is used by embodiments of the present invention.

Figure 6:
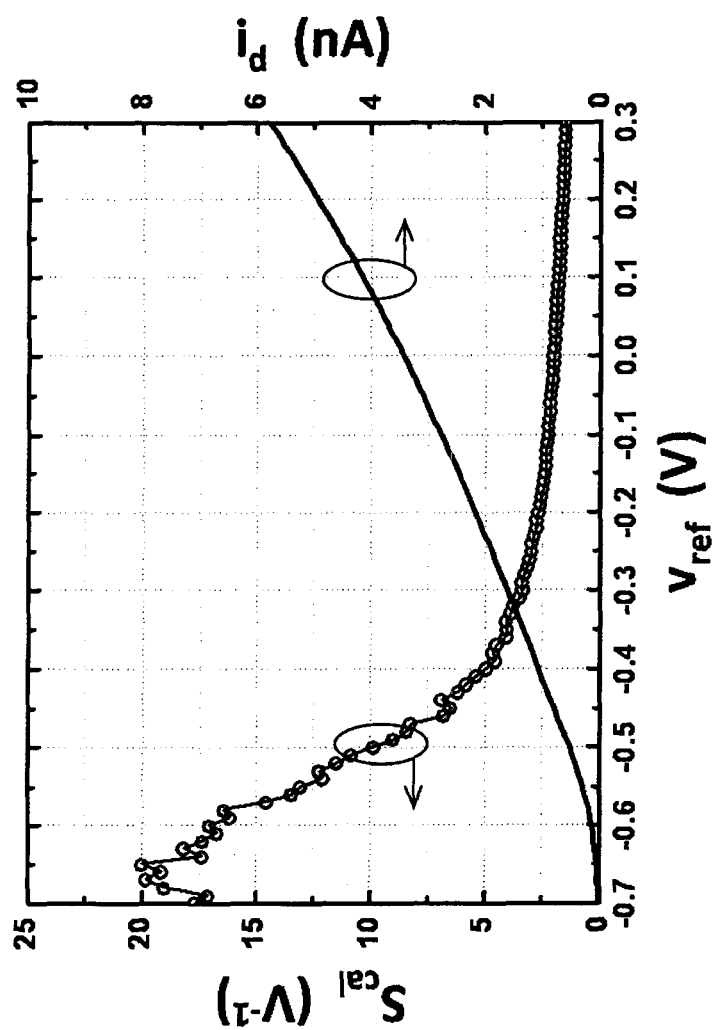
FIG. 6 shows a diagram indicating a measurement of the sensitivity of the biosensor over the reference voltage as well as the source/drain current over the reference voltage.

FIG. 6 shows a diagram indicating a measurement of the sensitivity $S_{cal}$ of the biosensor 100 over the reference voltage $V_{REF}$ as well as the source/drain current $I_D$ over the reference voltage $V_{REF}$. As can be derived from FIG. 6, the sensitivity $S_{cal}$ reaches a maximum at low reference voltages $V_{REF}$ (subthreshold region). However, at low reference voltages $V_{REF}$, the source/drain current $I_D$ becomes very small. At very low reference voltages $V_{REF}$, the source/drain current $I_D$ may thus be too small in order to yield reproducible results. Thus, the reference voltage $V_{REF}$ should be chosen such that the both the sensitivity $S_{cal}$ and the source/drain current $I_D$ have acceptable values.

Figure 9:
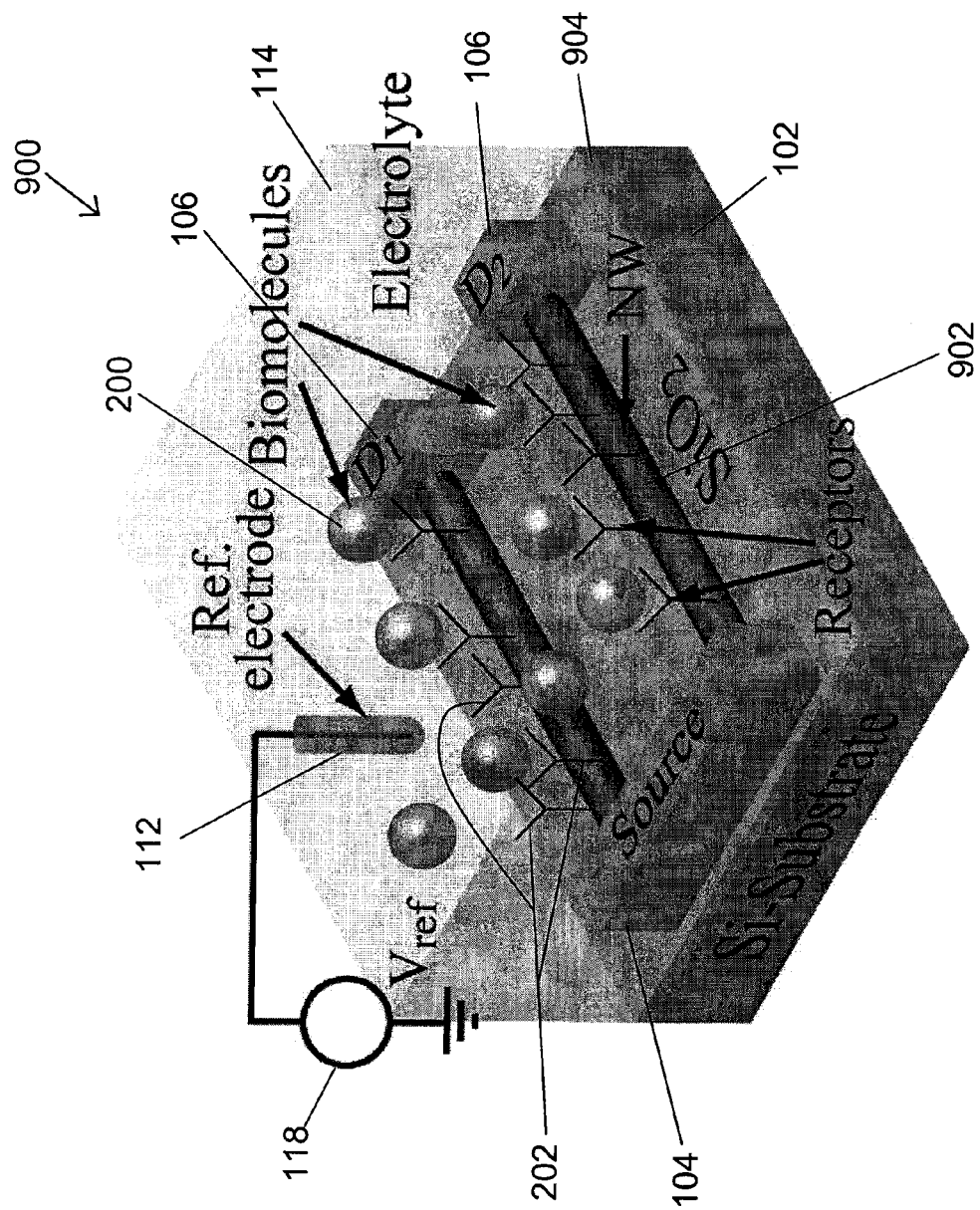
FIG. 9 shows a schematic view of a biosensor which may be calibrated according to an embodiment.

FIG. 9 shows a further possible biosensor 900 which may be calibrated according to embodiments of the present invention. In contrast to the biosensor 100 which is a field effect transistor (FET) biosensor, biosensor 900 is a nanowire biosensor. Instead of the channel area 108, the biosensor 900 uses nanowires 902 which extend between one or several source areas 104 and one or several drain areas 106. On the nanowires 902, receptors 202 are located which are adapted to bind target molecules 200 of a particular kind. The substrate 102 is isolated against the source areas 104, the nanowires 902 and the drain areas 106 via an isolation layer 904. The measuring of the sensitivity of the biosensor 900 is carried out in an analogue manner as described in the context of FIG. 1B. In this context, it should be noted that, in the scope of the present invention, the term "field effect biosensor" includes both biosensors as shown in FIG. 1 ("classical" filed effect biosensor) and biosensors an shown FIG. 9 (nanowire biosensor). The nanowire biosensor as shown in FIG. 9 is a filed effect device in the sense that an electrical field controls the transmissivity through the nanowires.

Figure 10:
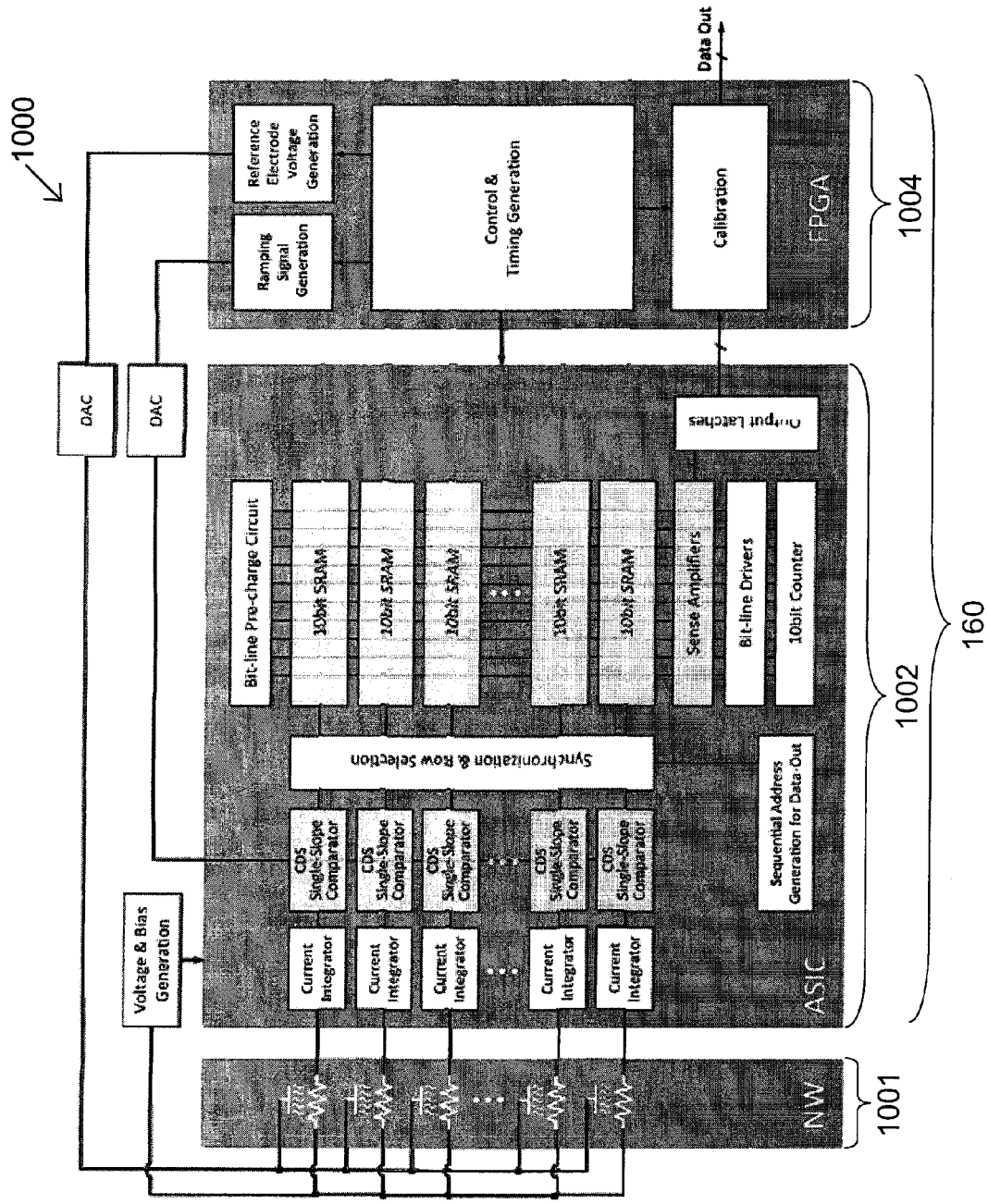
FIG. 10 shows a schematic drawing of a circuitry usable in conjunction with the biosensors in order to carry out the inventive method according to an embodiment of the present invention.

In FIG. 10, a possible embodiment 1000 of the processing/controlling unit 160 is given. It is assumed in this example that the processing/controlling unit 160 controls a plurality of biosensors at the same time. The plurality of biosensors are indicated by block 1001. In this example, the processing/controlling unit 160 comprises an ASIC unit 1002 and a FPGA unit 1004. The ASIC unit 1002 comprises a plurality of channels, each channel being connected to one of the biosensors. Each channel further comprises a pixel circuit which processes the output (a plurality of source/drain currents $I_D$) of the biosensors. The FPGA unit 1004 controls the interaction between the ASIC unit 1002 and the plurality of biosensors 1002. Further, the FPGA unit 1004 processes the data collected by the ASIC unit 1002 and generates and outputs calibrated biosensor data.

Figure 11:
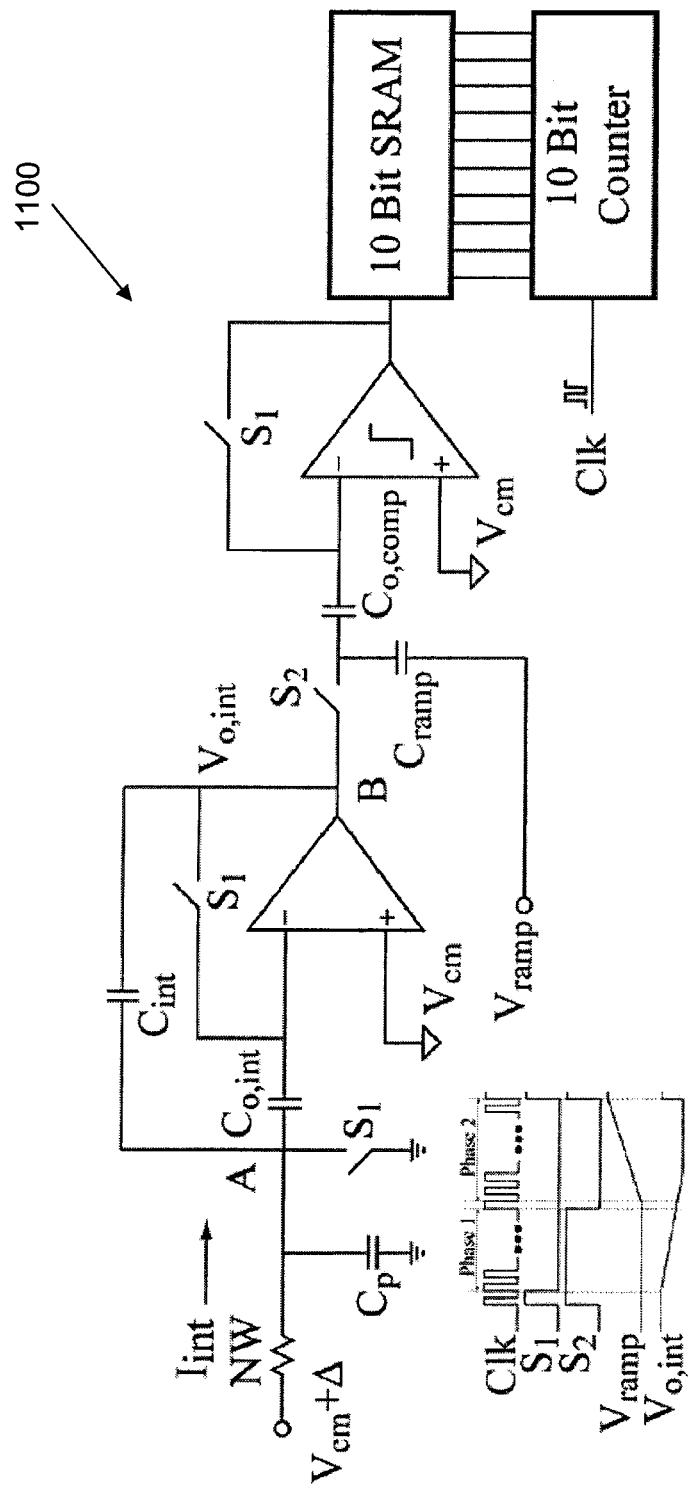
FIG. 11 shows a schematic drawing of a circuitry usable in conjunction with the circuitry shown in FIG. 10 according to an embodiment of the present invention.

An example of a pixel circuit 1100 which may be employed in the ASIC unit 1002 is shown in FIG. 11.

According to an embodiment of the present invention, determining the sensitivity of a field effect biosensor comprises: determining an effective transconductance function by differentiating the measured drain current function with respect to the reference voltage supplied; dividing the determined effective transconductance function by the measured drain current function.

According to an embodiment of the present invention, the sensitivities of the different field effect biosensors are compared among each other, wherein a normalization process is carried out in which an average sensitivity for all of the field effect biosensors is calculated.

According to an embodiment of the present invention, the working point of each field effect biosensor is shifted into a region of maximum sensitivity.

According to an embodiment of the present invention, the working point of each field effect biosensor is shifted into a region of increased sensitivity in which the sensitivity is not maximum, in which however the drain current would still be large enough to yield reliable measurement results.

According to an embodiment of the present invention, the sensitivities of the field effect biosensors are compared among each other, wherein biosensors showing a sensitivity falling below a first threshold value or exceeding a second threshold value are disabled.

According to an embodiment of the present invention, the sensitivity determining unit is further adapted to determine an effective transconductance function by differentiating the measured drain current function with respect to reference voltage supplied to the reference electrode; and dividing the determined effective transconductance function by the measured drain current function.

According to an embodiment of the present invention, the sensitivity determining/adjusting system comprises a processing unit adapted to compare the sensitivities of the field effect biosensors among each other, wherein a normalization process is carried out in which an average sensitivity for all of the field effect biosensors is calculated.

According to an embodiment of the present invention, the sensitivity determining/adjusting system comprises a calibration unit adapted to shift the working point of each field effect biosensor into a region of maximum sensitivity.

According to an embodiment of the present invention, the sensitivity determining/adjusting system comprises a calibration unit adapted to shift the working point of each field effect biosensor into a region of increased sensitivity in which the sensitivity is not maximum, in which however the drain current would still be large enough to yield reliable measurement results.

According to an embodiment of the present invention, the sensitivity determining/adjusting system comprises a disabling unit adapted to compare the sensitivities of the field effect biosensors among each other, wherein biosensors showing a sensitivity falling below a first threshold value or exceeding a second threshold value are disabled.

In the following description, further background information/aspects of the present invention will be given.

The calibration technique according to embodiments of the present invention originates from the finding that the biosensing sensitivity is well presented by the effective transconductance parameter ($\Delta i_d / \Delta v_{ref}$) of the field-effect sensor device, which is measured as a drain current change ($\Delta i_d$) when the reference electrode voltage increments ($\Delta v_{ref}$). This observation will be proven by the following analysis, and the theoretical background and operational details of the proposed calibration scheme will be explained as well.

The simplified diagram of a planar field-effect sensor device and its biosensing setup is depicted in FIG. 1A/1B. Note that the sensor device is very similar to a typical MOSFET device, except the conductive gate of the MOSFET is replaced by the combination of an electrolytic solution and a reference electrode. The surface of the exposed gate insulator is functionalized, then probe molecules are immobilized on this surface. On successful binding with the target molecules, depending on the effective charge of the target molecules, a positive or negative shift in the threshold voltage of the FET is detected.

FIG. 2 shows a 1-D model of the device together with the charge distribution and energy band diagram [see reference 1]. The charge balance between the semiconductor and electrolyte bulk required by Gauss' law is given by $$q_s + q_0 + q_{md} = 0 \qquad (1)$$

wherein a charge density $q_{md}$ can be split into a molecular charge density $q_m$ from the molecules on the exposed gate insulator surface and $q_d$ due to the ion distribution in the bulk electrolyte, $g_0$ is the surface charge density at the insulator surface due to the proton exchange at amphoteric sites, and $q_s$ is the semiconductor charge density. Several characteristic electrostatic potential drops linked with the distribution of aforementioned charge components can be noticed: (a) $\psi_d$ due to $q_d$, (b) $\psi_{md}$ due to $g_{md}$, (c) $\psi_0$ due to $q_{md}$ and $g_0$, (d) $\psi_s$ due to $g_s$, (e) $\psi_{cl}$ and $\psi_{ins}$ due to $q_{md}$, $g_0$, and $q_s$. These associations between the electrostatic potentials and charge components can be modeled as a set of capacitances connected to each other as shown in FIG. 3. $C_{g,FET}$, $C_{cl}$, $C_{stern}$ and $C_{dl}$ are the gate capacitance of the field-effect biosensor, cover layer capacitance, Stern layer capacitance and Guoy-Chapman double layer capacitance, respectively [see reference 1] and are defined as follow:

$$C_{g,FET} = \frac{C_{ins}C_s}{C_{ins} + C_s} \qquad (2)$$

$$C_s = \frac{\partial q_s}{\partial \psi_s} \qquad (3)$$

$$C_{ins} = \frac{\partial q_s}{\partial \psi_{ins}} \qquad (4)$$

$$C_{cl} = \frac{\partial (q_{md} + q_0)}{\partial \psi_{cl}} \qquad (5)$$

$$C_0 = \frac{\partial q_0}{\partial \psi_0} \qquad (6)$$

$$C_{stern} = \frac{\partial q_{md}}{\partial (\psi_{md} - \psi_0)} \qquad (7)$$

$$C_{dl} = \frac{\partial q_{md}}{\partial \psi_{md}}. \qquad (8)$$

A Warburg impedance $R_{dl}$ of the insulator-electrolyte interface and the bulk electrolyte resistance $R_{be}$ have been neglected in this model. Generally, this omission is justified at low frequencies and at low bias potentials [see reference 2]. The $g_{m,FET}$ represents the transconductance of the field-effect device.

Based on the derived model, the sensitivity of biosensor to the molecular charges can be analyzed (FIG. 4). The body and source terminals of the device are grounded, the reference electrode is biased at a certain fixed voltage, and the drain terminal is biased with a small voltage to induce the flow of drain current $i_d$. When molecular charge $\Delta q_m$ is added, the gate potential of the device changes through the capacitive network, and in turn the $i_d$ changes to $i_d + \Delta i_d$. The sensitivity to the molecular charge $S_{qm}$ is defined by $$S_{qm} \equiv \frac{\Delta i_d / i_d}{\Delta q_m} \qquad (9)$$

and can be expressed as follows:

$$S_{qm} = \frac{\Delta v_g}{\Delta q_m} \times \frac{\Delta i_d}{\Delta v_g} \times \frac{1}{i_d} = \frac{\Delta v_g}{\Delta q_m} \times \frac{g_{m,FET}}{i_d}. \qquad (10)$$

Assuming that $C_{g,FET}$ and $C_{cl}$ are much smaller than $C_0$ and $C_{stern}$ as is typically true, the gate voltage change due to the molecular charge increment becomes $$\frac{\Delta v_g}{\Delta q_m} \approx \frac{1}{C_{dl} + \frac{C_{stern}C_0}{C_{stern} + C_0}} \cdot \frac{C_{stern}}{C_{stern} + C_0} \cdot \frac{C_{cl}}{C_{cl} + C_{g,FET}} \qquad (11)$$

$$= \frac{C_{stern}}{C_{dl}C_{stern} + C_{dl}C_0 + C_{stern}C_0} \cdot \frac{C_{cl}}{C_{cl} + C_{g,FET}}.$$

As a result, the $S_{qm}$ is given by $$S_{qm} = \frac{C_{stern}}{C_{dl}C_{stern} + C_{dl}C_0 + C_{stern}C_0} \cdot \frac{C_{cl}}{C_{cl} + C_{g,FET}} \cdot \frac{g_{m,FET}}{i_d}. \qquad (12)$$

In the calibration process, however, the actual sensitivity to the molecular charge cannot be measured directly. Embodiments of the present invention propose using a small-signal change in the reference voltage instead of the real molecular charge attachment to estimate the sensitivity to the molecular charge so that the sensor device sensitivity can be calibrated. FIG. 5 shows the setup for measuring the sensitivity to the reference voltage change $\Delta v_{ref}$. This sensitivity characterized for calibration purpose $S_{cal}$ is defined by $$S_{cal} = S_{vref} \equiv \frac{\Delta i_d / i_d}{\Delta v_{ref}} \qquad (13)$$

and can be written as $$S_{cal} = \frac{\Delta v_g}{\Delta v_{ref}} \times \frac{g_{m,FET}}{i_d} = \frac{g_{m,eff}}{i_d} = K_{cal} \cdot S_{qm} \qquad (14)$$

where the effective transconductance $g_{m,eff}$ is approximated by $$g_{m,eff} = \frac{\Delta v_g}{\Delta v_{ref}} \times g_{m,FET} \approx \frac{C_{cl}}{C_{cl} + C_{g,FET}} \cdot g_{m,FET} \qquad (15)$$

with assuming $C_{g,FET}$ and $C_{cl}$ are much smaller than $C_0$ and $C_{stern}$. The $K_{cal}$ which is the proportionality factor between the $S_{cal}$ and $S_{qm}$ can be written as $$K_{cal} = \frac{S_{cal}}{S_{qm}} \approx \frac{C_{dl}C_{stern} + C_{dl}C_0 + C_{stern}C_0}{C_{stern}} \qquad (16)$$

Note that of $C_{dl}$, $C_{stern}$, and $C_0$ are all very weak function of $v_{ref}$ compared to $g_{m,FET}$ in the operation range of interest [see reference 2], and therefore $K_{cal}$ can be regarded as a constant. It implies that $S_{cal}$ based on the measurement of the effective transconductance $g_{m,eff}$ and drain current $i_d$ provides a good representation of the actual biosensing sensitivity $S_{qm}$, and can be effectively used for the calibration process.

Based on the observation discussed above, according to an embodiment of the present invention, a new calibration technique as follows is proposed: (a) For a biosensor or a multitude of biosensors, $i_d$ is measured with sweeping $v_{ref}$ over the range of interest, e.g. −0.5 to +0.5 V. (b) For each sensor, $g_{m,eff}$ is calculated as a function of $v_{ref}$ by differentiating the measured $i_d$ with respect to $V_{ref}$. (c) For each sensor, $S_{cal}$ is calculated by dividing the calculated $g_{m,eff}$ by the measured $i_d$.

(d) The calculated $S_{cal}$ can be used for normalization of the results among different sensors, or for the calibration by using the result from the biosensor placed in the separate control chamber where the known concentration of the analyte is applied. Note that this technique can be used not only for the normalization or calibration but also for the optimization of the sensor sensitivity.

As shown in FIG. 6, $S_{cal}=g_{m,eff}/i_d$ increases as $v_{ref}$ decreases and comes saturated in the subthreshold region of the device, meaning that if the biosensor is operated in the subthreshold region, the sensitivity can be maximized. However, it should be considered that in the deep subthreshold region, $i_d$ becomes too small to be measured reliably, and therefore, according to an embodiment of the present invention, the optimum $v_{ref}$ may be decided considering both the maximization of $S_{cal}$ and the current measurement limit of the readout system used. Another application of the proposed technique is the screening of the biosensor devices among many. For example, if the measured $S_{cal}$ of a certain device is lower than the preset threshold, the result from this device can be discarded for better overall statistics.

Figure 7:
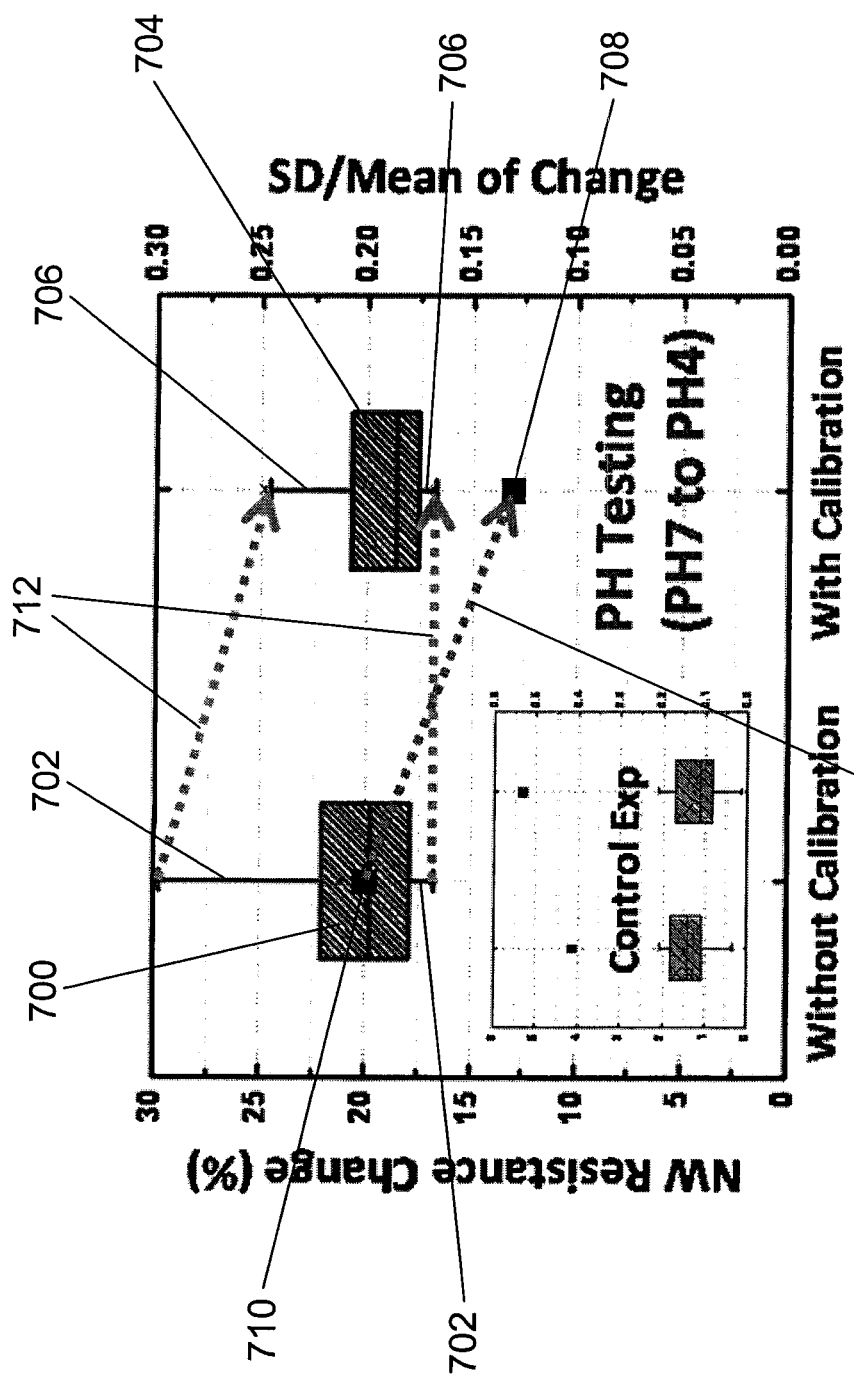
FIG. 7 shows measurement results of pH testing with and without applying the inventive method.
Figure 8:
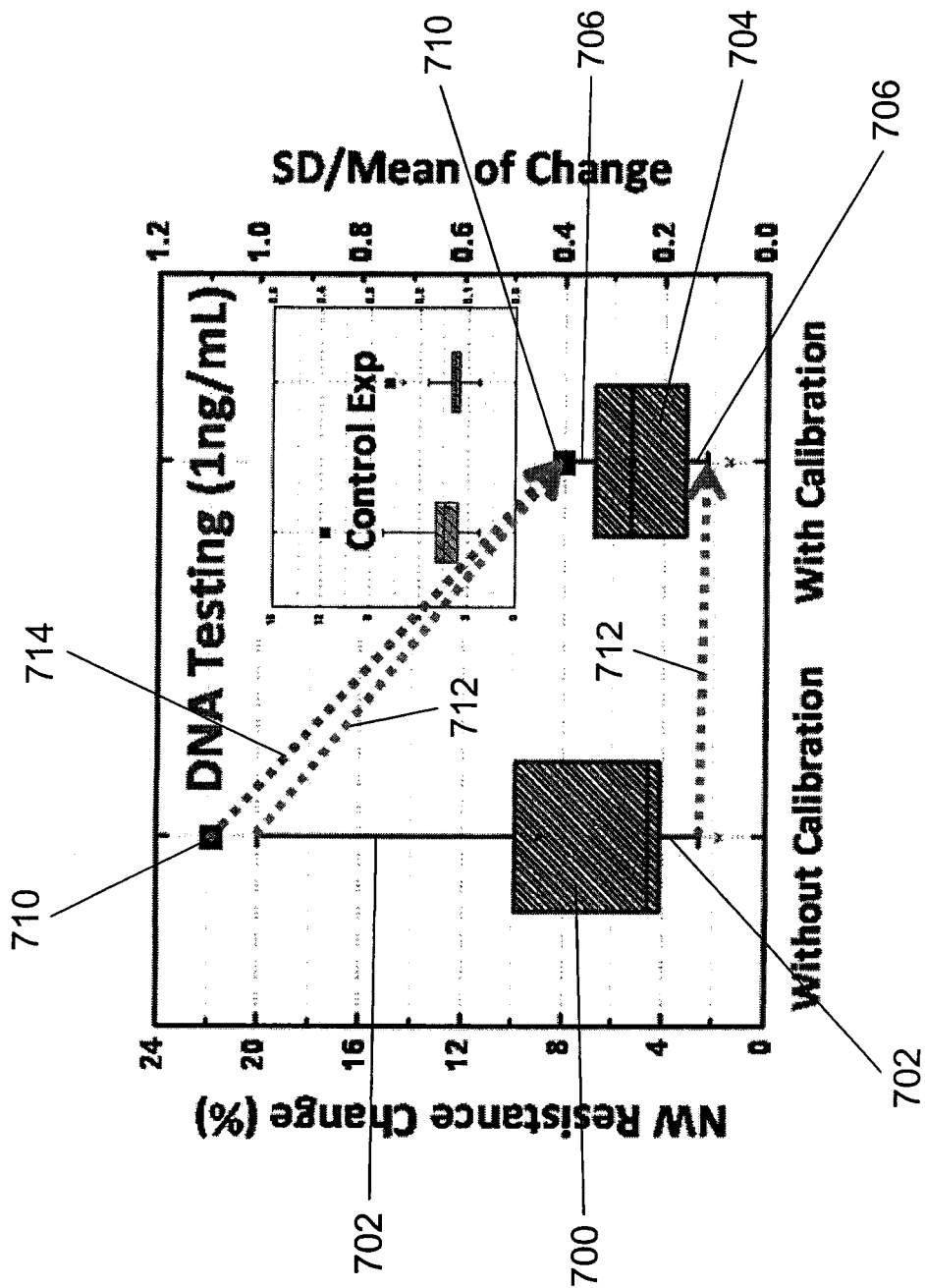
FIG. 8 shows measurement results of DNA testing with and without applying the inventive method.

In order to validate the proposed calibration technique, pH testing and DNA testing were performed on nanowire biosensors, one popular type of nano-scale field-effect biosensors [see reference 3]. In the pH testing, the pH level changed from 7 to 4 and the corresponding nanowire resistance change was measured from a total of 30 nanowire biosensors. As shown in FIG. 7, by applying the calibration technique, the data statistics becomes much improved. As an indicator of the measured data spread, the ratio of the standard deviation and the mean of resistance change was calculated. This measure of data spread is reduced from 0.2 to 0.13 with applying the calibration technique. The same improvement was observed in the DNA testing performed, see FIG. 8. In this experiment, after applying the 1 ng/mL of the target DNA, the corresponding nanowire resistance change was measured again from 30 nanowire biosensors. The ratio of the standard deviation and the mean of resistance change decreases from 1.1 to 0.4 with the proposed technique applied. In FIGS. 7 and 8, box 700 indicates the nanowire resistance change in % measured without calibration, and bars 702 the corresponding error bars, box 704 indicates the nanowire resistance change in % measured with calibration, and bars 706 the corresponding error bars, square dots 710 the SD/mean of change, arrows 712 indicate the improvement of the error bars, arrow 714 the improvement of the SD/mean of change.

According to an embodiment of the present invention, the calibration factor $S_{cal}$ is based on the measurement of the effective transconductance $g_{m,eff}$ and the drain current $i_d$, wherein the calibration technique is as follows: For a biosensor or a multitude of biosensors, $i_d$ is measured with sweeping $v_{ref}$ over the range of interest, e.g. −0.7 to +0.3V; the $g_{m,eff}$ is calculated as a function of $v_{ref}$ by differentiating the measured $i_d$ with respect to $v_{ref}$ and the value of $S_{cal}$ is calculated as for each biosensor. Subsequently, $S_{cal}$ can be used for normalization of the results among different sensors. Note that this technique can be used not only for the normalization or calibration but also for the optimization of the sensor sensitivity. The value of $S_{cal}$ increases as $v_{ref}$ decreases and peaks in the subthreshold region of the biosensor, hence operating in the subthreshold region can maximize the sensitivity. However, it should be considered that in the deep subthreshold region, $i_d$ becomes too small to be measured reliably, and therefore the optimum $v_{ref}$ may be decided considering both the maximization of $S_{cal}$ and the current measurement limit of the readout system used.

Returning to FIG. 10, an embodiment of an overall readout system is shown which comprises 256 channels readout ASIC (application specific integrated circuit) 1002 and an FPGA (Field Programmable Gate Array) 1004. Each channel in the ASIC is assigned with a dedicated pixel circuit block containing low current sensing circuits and a bit single slope ADC. The FPGA is implemented to provide the timing controls for proper operation of the ASIC and to be used during calibration to calculate for the factor $g_{m,eff}$, $S_{cal}$ and the resultant sensitivity factor $S_{qm}$. FIG. 11 shows a possible embodiment of each pixel circuit. Low current sensing is achieved with the single-ended charge integrator followed by the correlated double sampling (CDS) circuit which helps to reduce the offset and the 1/f noise contribution from the charge integrator. The CDS circuit setup with the comparator is combined with a 10-bit SRAM and counter circuits to form a single-slope ADC architecture to provide the digital readout for the current measured at the input of the charge integrator. Both the charge integrator and the comparator are implemented with an offset cancellation scheme using the switch $S_1$. When switch $S_1$ is closed, the offset voltage from the charge integrator and the comparator is stored on the capacitor $C_{off}$ and $C_{o,comp}$, respectively. The function of capacitor $C_{ramp}$ is to capture the offset from the ramp input. Subsequently, when switch $S_1$ is opened, the offset is cancelled. The output voltage of the charge integrator is directly proportional to the input current $i_{int}$ integrated across the capacitor $C_{int}$. The period of the integration as represented by Phase 1 (FIG. 11) is adjustable externally to fit different input current ranges. Switch $S_2$ is kept closed during integration period (Phase 1) and open in the Phase 2. Phase 2 is the analog to digital conversation period where a rising ramp signal is applied via the capacitor $C_{ramp}$. At the same time, the counter is also initiated. The rising ramp signal toggles the output of the comparator at the point where the voltage at the negative input of the comparator is larger than $V_{cm}$. Consequently, the SRAM will capture the count on the counter. The count captured on the SRAM is the digital representation of the input current $I_{int}$.

Figure 12:
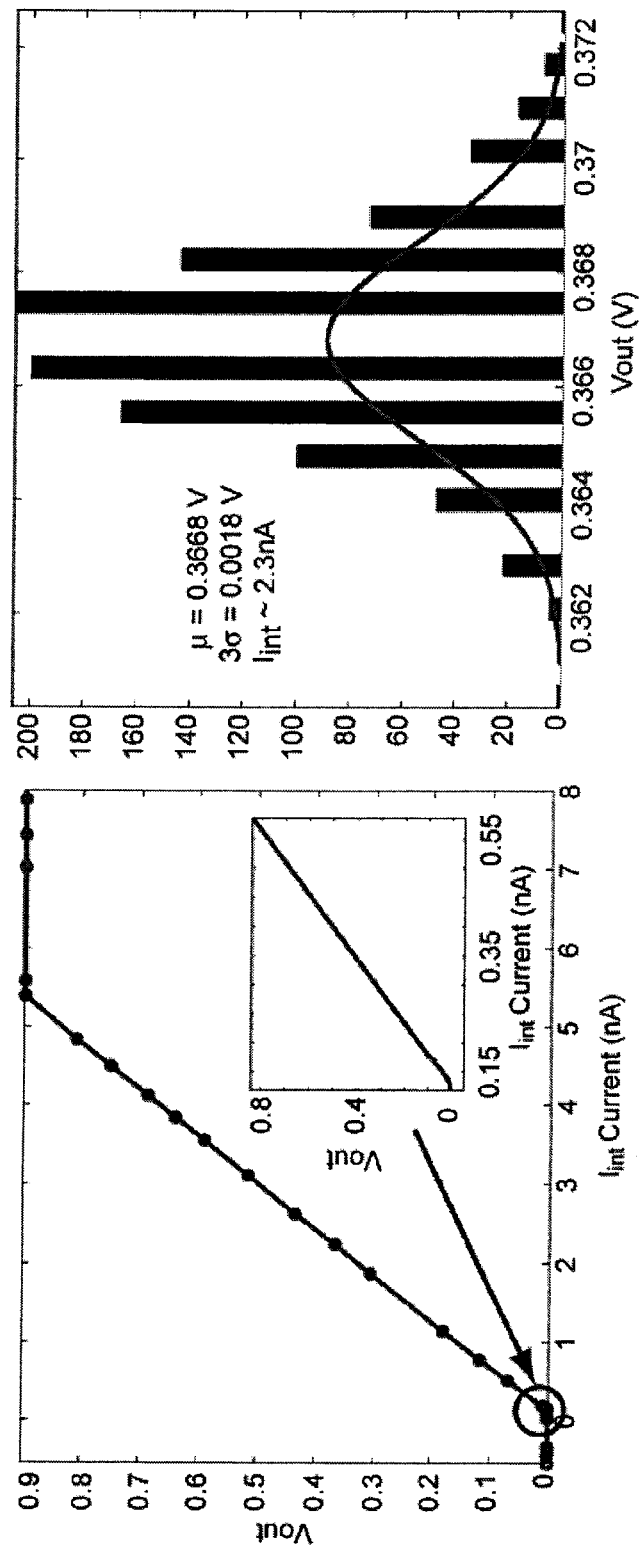
FIG. 12 shows experimental results obtained with the circuitry shown in FIG. 10.

FIG. 12 shows initial electrical measurements made with the ASIC. The electrical measurements were obtained by sweeping the input current range from 100 pA to 8 nA for an integration period of 1.5 ms. $V_{out}$ is the converted digital output with respect to the different input current $I_{int}$. The results show good linearity output response across the 40 dB of input current range. The dynamic range tested is sufficient for the intended application of interest but is not limited to only 40 dB as it can be further increased by the adjustment of the integration period as mentioned previously. The diagram on the right of FIG. 12 shows the output referred noise characteristic for the measured input current at 2.3 nA. The 95% percentile or 3 standard deviation concludes an input noise variation of less than 0.5% or ±11.5 pA variation. This implies that the input referred noise floor for the measurement is 11.5 $pA_{rms}$ for the signal bandwidth of interest.

According to an embodiment of the present invention, a 256 channels readout system is used. It comprises a microfluidic housing that holds the 256 nanowire biosensors, a special electrical probe connector that allows connection to the nanowire biosensors and our readout ASIC. The ASIC chip was fabricated using Chartered 0.18 μm 1P6M standard CMOS technology with MIM capacitor option. Approximately 120,000 transistors are integrated on 4.6 mm×4.6 mm die area for the 64-channels of the amplifiers and A/D converters. The chip is powered up with 1.8V VDD and consumes 1.8 mW of power.

According to one embodiment of the present invention, the nanowire biosensor was covalently immobilized with peptide nucleic acid (PNA), a bifunctional linker, glutaraldehyde, was employed to bind its one end to the SiNW amines, leaving the other end to bind amine-terminated PNA. The nanowire biosensors were treated with 1% glutaraldehyde in $H_2O$ for 1 h, and rinsed with pure $H_2O$. Ten micromolars of PNA in 1×SSC were incubated with the SiNWs in a humid atmosphere at room temperature overnight. The chips were washed three times with 1×SSC, 5 min each after immobilization of the PNA. The freshly prepared chips were used for measurements immediately. FIG. 8 shows the results of the DNA binding on the nanowire biosensor. The results obtained are statistical averages measured across 20 nanowire biosensors. The consequence of the binding results in the change in the nanowire biosensor resistance. The spread of the measured resistance change is larger for case where no calibration was implemented where the coefficient of variation (CV) is 1.1. However, the CV value for case where calibration was implemented recorded a reduction to 0.4. This indicates that the calibration algorithm is able to improve on the measurement by first taking into account on the variability of the individual nanowire biosensor sensitivity and normalizing their final sensitivity with the appropriate $S_{cal}$ coefficient.

As has become apparent from the foregoing description, according to embodiments of the present invention, a new calibration technique based on the measurement of the effective transconductance parameter of the field-effect biosensors is provided. The technique can be used for normalization of the results among different sensors to mitigate the variability of their electrical properties, or for the calibration by using the result from the biosensor placed in the separate control chamber where the known concentration of the analyte is applied. The technique can be also used for the optimization of the sensor sensitivity, considering both the maximization of sensitivity and the current measurement limit of the readout system used. Another application of the proposed technique is the screening of the poor-quality biosensor devices among a plurality. In order to validate the proposed calibration technique, pH testing and DNA testing were performed on nanowire biosensors, and it was verified that the data statistics become much improved by applying the calibration technique.

As has become apparent from the forgoing description, embodiments of the calibration method according to the present invention use the effective transconductance parameter of field-effect sensor devices. This method is very effective because it directly calibrates the sensor sensitivity, and does not require any addition of substantial complexities—e.g. a set of calibration solutions for calibration curve construction, complicated on-chip calibration circuitry, special device structure, or complex calibration algorithm.

REFERENCES

[1] L. Bousse, *J. Chem. Phys.*, vol. 76, p. 5128, 1982.
[2] D. Landheer, G. Aers, W. R. McKinnon, M. J. Deen, J. C. Ranuarez, *J. Appl. Phys.*, vol. 98, p. 044701, 2005.
[3] G-J Zhang, J. H. Chua, R-E. Chee, A. Agarwal, S. M. Wong, K. D. Buddharaju, N. Balasubramanian, *Biosens. Bioelectron.*, vol. 23, p. 1701, 2008.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of determining/adjusting the sensitivity of a biosensor arrangement comprising at least one field effect biosensor, each of the at least one field effect biosensor comprising:
    a semiconductor substrate comprising a source region, a drain region and a channel region disposed between the source region and the drain region;
    a gate isolation layer covering the channel region; and
    a reference electrode disposed over the gate isolation layer such that a electrolytic solution to be sensed can be provided between the reference electrode and the gate isolation layer,
the method comprising the following processes carried out for each field effect biosensor:
    providing an electrolytic solution between the reference electrode and the gate isolation layer;
    applying a source/drain voltage between the source region and the drain region;
    varying a reference voltage supplied to the reference electrode over a voltage range;
    measuring a resulting drain current while varying the reference voltage in order to obtain a corresponding drain current function; and
    determining the sensitivity of the field effect biosensor based on the reference voltage supplied to the reference electrode and the corresponding drain current function, wherein determining the sensitivity of the field effect biosensor comprises
        determining an effective transconductance function by differentiating the measured drain current function with respect to the reference voltage supplied, and
        dividing the determined effective transconductance function by the measured drain current function.

2. The method according to claim 1,
further comprising comparing the sensitivities of the different field effect biosensors among each other, wherein a normalization process is carried out in which an average sensitivity for all of the field effect biosensors is calculated.

3. The method according to claim 1,
further comprising shifting the working point of each field effect biosensor into a region of maximum sensitivity.

4. The method according to claim 1,
further comprising shifting the working point of each field effect biosensor into a region of increased sensitivity in which the sensitivity is not maximum, in which however the drain current would still be large enough to yield reliable measurement results.

5. The method according to claim 1,
further comprising comparing the sensitivities of the field effect biosensors among each other, wherein biosensors showing a sensitivity falling below a first threshold value or exceeding a second threshold value are disabled.

6. A biosensor sensitivity determining system for determining/adjusting the sensitivity of a biosensor arrangement comprising at least one field effect biosensor, each of the at least one field effect biosensor comprising:
    a semiconductor substrate comprising a source region, a drain region and a channel region disposed between the source region and the drain region;

a gate isolation layer covering the channel region; and a reference electrode disposed over the gate isolation layer such that a electrolytic solution to be sensed can be provided between the reference electrode and the gate isolation layer, the biosensor sensitivity determining system comprising the following functional units for each of the field effect biosensors:

a source/drain voltage applying unit adapted to apply a source/drain voltage between the source region and the drain region;

a reference voltage applying unit adapted to apply a varying reference voltage which varies over a predetermined voltage range to the reference electrode;

a drain current measuring unit adapted to measure a drain current resulting when varying the reference voltage in order to obtain a corresponding drain current function; and a sensitivity determining unit adapted to determine the sensitivity based on the reference voltage supplied to the corresponding reference electrode and the corresponding drain current function, wherein the sensitivity determining unit is further adapted to determine an effective transconductance function by differentiating the measured drain current function with respect to reference voltage supplied to the reference electrode, and divide the determined effective transconductance function by the measured drain current function.

7. The biosensor sensitivity determining system according to claim 6, further comprising a processing unit adapted to compare the sensitivities of the field effect biosensors among each other, wherein a normalization process is carried out in which an average sensitivity for all of the field effect biosensors is calculated.

8. The biosensor sensitivity determining system according to claim 6, further comprising a calibration unit adapted to shift the working point of each field effect biosensor into a region of maximum sensitivity.

9. The biosensor sensitivity determining system according to claim 6, further comprising a calibration unit adapted to shift the working point of each field effect biosensor into a region of increased sensitivity in which the sensitivity is not maximum, in which however the drain current would still be large enough to yield reliable measurement results.

10. The biosensor sensitivity determining system according to claim 6, further comprising a disabling unit adapted to compare the sensitivities of the field effect biosensors among each other, wherein biosensors showing a sensitivity falling below a first threshold value or exceeding a second threshold value are disabled.

11. A method of determining/adjusting the sensitivity of a biosensor arrangement comprising at least one biosensor, each of the at least one biosensor comprising:

a semiconductor substrate comprising a source region and a drain region;

an isolation layer covering a region between the source region and the drain region; and a reference electrode disposed over the isolation layer such that a electrolytic solution to be sensed can be provided between the reference electrode and the isolation layer, the method comprising the following processes carried out for each biosensor:

providing an electrolytic solution between the reference electrode and the isolation layer;

applying a source/drain voltage between the source region and the drain region;

varying a reference voltage supplied to the reference electrode over a voltage range;

measuring a resulting drain current while varying the reference voltage in order to obtain a corresponding drain current function; and determining the sensitivity of the biosensor based on the reference voltage supplied to the reference electrode and the corresponding drain current function, wherein determining the sensitivity of the biosensor comprises determining an effective transconductance function by differentiating the measured drain current function with respect to the reference voltage supplied, and dividing the determined effective transconductance function by the measured drain current function.

12. The method according to claim 11, further comprising at least one nanowire extends between the source region and the drain region.

13. The method according to claim 12, wherein the isolation layer isolates the at least one nanowire from the substrate.

14. A biosensor sensitivity determining system for determining/adjusting the sensitivity of a biosensor arrangement comprising at least one biosensor, each of the at least one biosensor comprising:

a semiconductor substrate comprising a source region and a drain region;

an isolation layer covering a region between the source region and the drain region; and a reference electrode disposed over the isolation layer such that a electrolytic solution to be sensed can be provided between the reference electrode and the isolation layer, the biosensor sensitivity determining system comprising the following functional units for each of the biosensors:

a source/drain voltage applying unit adapted to apply a source/drain voltage between the source region and the drain region;

a reference voltage applying unit adapted to apply a varying reference voltage which varies over a predetermined voltage range to the reference electrode;

a drain current measuring unit adapted to measure a drain current resulting when varying the reference voltage in order to obtain a corresponding drain current function; and a sensitivity determining unit adapted to determine the sensitivity based on the reference voltage supplied to the corresponding reference electrode and the corresponding drain current function, wherein the sensitivity determining unit is further adapted to determine an effective transconductance function by differentiating the measured drain current function with respect to reference voltage supplied to the reference electrode, and divide the determined effective transconductance function by the measured drain current function.

15. The biosensor sensitivity determining system according to claim 14, further comprising at least one nanowire extends between the source region and the drain region.

16. The biosensor sensitivity determining system according to claim 15, wherein the isolation layer isolates the at least one nanowire from the substrate.

* * * * *